United States Patent

Muller et al.

[11] Patent Number: 5,919,408
[45] Date of Patent: Jul. 6, 1999

[54] PROCESS FOR THE PRODUCTION OF PSEUDOLATICES AND MICRO- OR NANOPARTICLES AND PHARMACEUTICAL PREPARATIONS CONTAINING THEM

[75] Inventors: Bernd W. Muller, Flintbek; Felix Junis-Specht, Dansch-Nienhof, both of Germany

[73] Assignee: Pharmatech GmbH, Germany

[21] Appl. No.: 08/531,283

[22] Filed: Sep. 20, 1995

Related U.S. Application Data

[63] Continuation of application No. 08/171,476, Dec. 23, 1993, abandoned.

[30] Foreign Application Priority Data

Dec. 24, 1992 [DE] Germany .......................... 42 44 466

[51] Int. Cl.⁶ .................. C08J 3/12; C08J 3/16
[52] U.S. Cl. .................. 264/5; 241/23; 241/29; 264/4.4; 424/484; 424/489; 424/499; 424/500; 424/501
[58] Field of Search .................. 424/489, 499, 424/500, 501, 484, 485, 486, 487, 488; 264/7, 8, 4.1, 4.4, 5; 241/29, 23

[56] References Cited

U.S. PATENT DOCUMENTS

| | | | |
|---|---|---|---|
| 3,893,967 | 7/1975 | Sunder-Plassman et al. . | |
| 4,853,434 | 8/1989 | Block . | |
| 5,100,591 | 3/1992 | Leclef et al. | 264/4.6 |
| 5,126,147 | 6/1992 | Silvestri et al. | 424/489 |
| 5,298,243 | 3/1994 | Ikada et al. | 424/85.1 |
| 5,326,572 | 7/1994 | Mehra et al. | 424/484 |

FOREIGN PATENT DOCUMENTS

| | | |
|---|---|---|
| 69481/91 | 7/1991 | Australia . |
| 0 167 825 | 1/1986 | European Pat. Off. . |
| 0 526 666 | 2/1993 | European Pat. Off. . |
| 3916020 | 11/1990 | Germany . |
| 3916020 A1 | 11/1990 | Germany . |
| wo 91/07171 | 5/1991 | WIPO . |

OTHER PUBLICATIONS

Rompp Chemie Lexicon. Edited by Falbe et al. Published by Georg Thieme Verlag. 9th Edition 1992. p. 4804. Full translation.

Rompp Chemie Lexikon. 9 Auflage. Georg Thieme Verlag. p. 4804.

Jepson Bolton's International Catalogue.

Rompp Chemie Lexikon 9 Auflage. Georg Thieme Verlag. p. 4804.

Evelyn B. Draper and Charles H. Becker, "Some Wax Formulations of Sulfaethylthiadiazole Produced by Aqueous Dispersion for Prolonged–Release Medication," *Journal of Pharmaceutical Sciences*, vol. 55, No. 4, Apr. 1966, pp. 376–380.

*Primary Examiner*—Robert H. Harrison
*Attorney, Agent, or Firm*—Nixon & Vanderhye

[57] ABSTRACT

The invention relates to a process for the production of pseudolatices or micro- and/or nanoparticles, in which a polymer is crystalline, partially crystalline or amorphous, is selected from cellulose derivatives, poly(meth)acrylates, shellac, polylactides, polylactide/polyglycolide mixtures, polyhydroxy butyric acids or polycyanoacrylates and is heated to a temperature above its glass transition temperature and then high-pressure homogenized in water or an aqueous buffer solution and this suspension is converted, if necessary, into micro- and/or nanoparticles by drying. Medicaments can be worked into the pseudolatices, micro- and/or nanoparticles.

12 Claims, 3 Drawing Sheets

PROCESS FOR THE PRODUCTION OF PSEUDOLATICES AND MICRO- OR NANOPARTICLES AND PHARMACEUTICAL PREPARATIONS CONTAINING THEM

This is a continuation of application Ser. No. 08/171,476, filed Dec. 23, 1993, now abandoned.

BACKGROUND OF THE INVENTION

The invention relates to a process for the production of pseudolatices and micro- or nanoparticles, their use and pharmaceutical preparations containing such pseudolatices or micro- or nanoparticles.

Usually, systems described as pseudolatices are those which are obtained by emulsifying organic polymer solutions in water and removing the solvents (G. S. Banker, G. E. Peck, Pharm. Technol. 5 (1981)). The recent production of pseudolatices is therefore mainly based on a corresponding process which was developed especially for cellulose derivatives (A. M. Ortega, dissertation, Purdue University, West Lafayette (USA) (1977)).

In view of the toxicity, the costs and the environmentally-damaging character of organic solvents, it was attempted to avoid processing polymers in such organic solvents.

For this reason, disperse, aqueous systems of some polymers were developed in the past, for example of cellulose derivatives and polymethacrylates.

Various routes were followed for this:

Development of emulsion polymerisates based on methacrylate (K. Lehmann, D. Dreher, Pharm. Ind. 34, 894 (1972)).

Partial replacement of organic solvents in aqueous organic plastics emulsions (K. H. Bauer, H. Osterwald, Pharm. Ind. 41, 1203 (1979)).

Use of plastics dispersions together with auxiliaries soluble in water or in alkali (W. Rohte, G. Groppenbächer, Pharm. Ind. 34, 892 (1972)).

Emulsification in organic solvents of dissolved cellulose derivatives in water and removal of the solvents (A. M. Ortega, dissertation, Purdue University, West Lafayette (USA) (1977)).

Direct emulsification of hydrophilic methacrylates in water (K. Lehmann, Acta Pharm. Technol. 32, 146 (1986)).

Dispersion of micronised polymers in aqueous solutions of plasticizers and film-coating at higher temperatures by thermal alloying (K. H. Bauer, H. Osterwald, Acta Pharm. Technol. 27, 99 (1986)).

Use of the aqueous solutions of salts of anionic polymerisates using volatile bases (K. H. Frömming, K. P. Krahl, Pharm. Ind. 43, 863 (1981)) or post-treating with acids (U.S. Pat. No. 4,017,647).

At low temperatures polymers are often hard, rigid solids. On heating, the polymer material receives enough thermal energy for its chains to be able to move. Above the melting temperature, the polymer behaves like a viscous liquid (provided there is no degradation). In the transition from the solid vitreous state to the liquid state, various intermediate states are passed through.

With crystalline polymers, an equilibrium between the solid and liquid states exists at the melting point. With crystalline substances, the molecular movement at the melting point rises rapidly from a relatively low level to a high level. In contrast, amorphous polymers behave differently. The molecular movement here increases slowly in several stages with increasing temperature. In contrast to crystalline polymers, in the case of amorphous or partially crystalline polymers not two, but several, different transition temperature ranges are to be noted. There are often 5 viscoelasticity ranges, e.g. in the case of polystyrene (J. M. G. Cowie, Chemie und Physik der Polymeren, Verlag Chemie (1976)).

The temperature at which a polymer changes from the vitreous state into the elastic state is called the glass transition temperature. A much-used method for determining the glass transition temperature is differential thermal analysis (DSC method) (W. C. Stanger, J. K. Guillory, J. Pharm. Sci. 68, 1005 (1979)).

Figure 1:
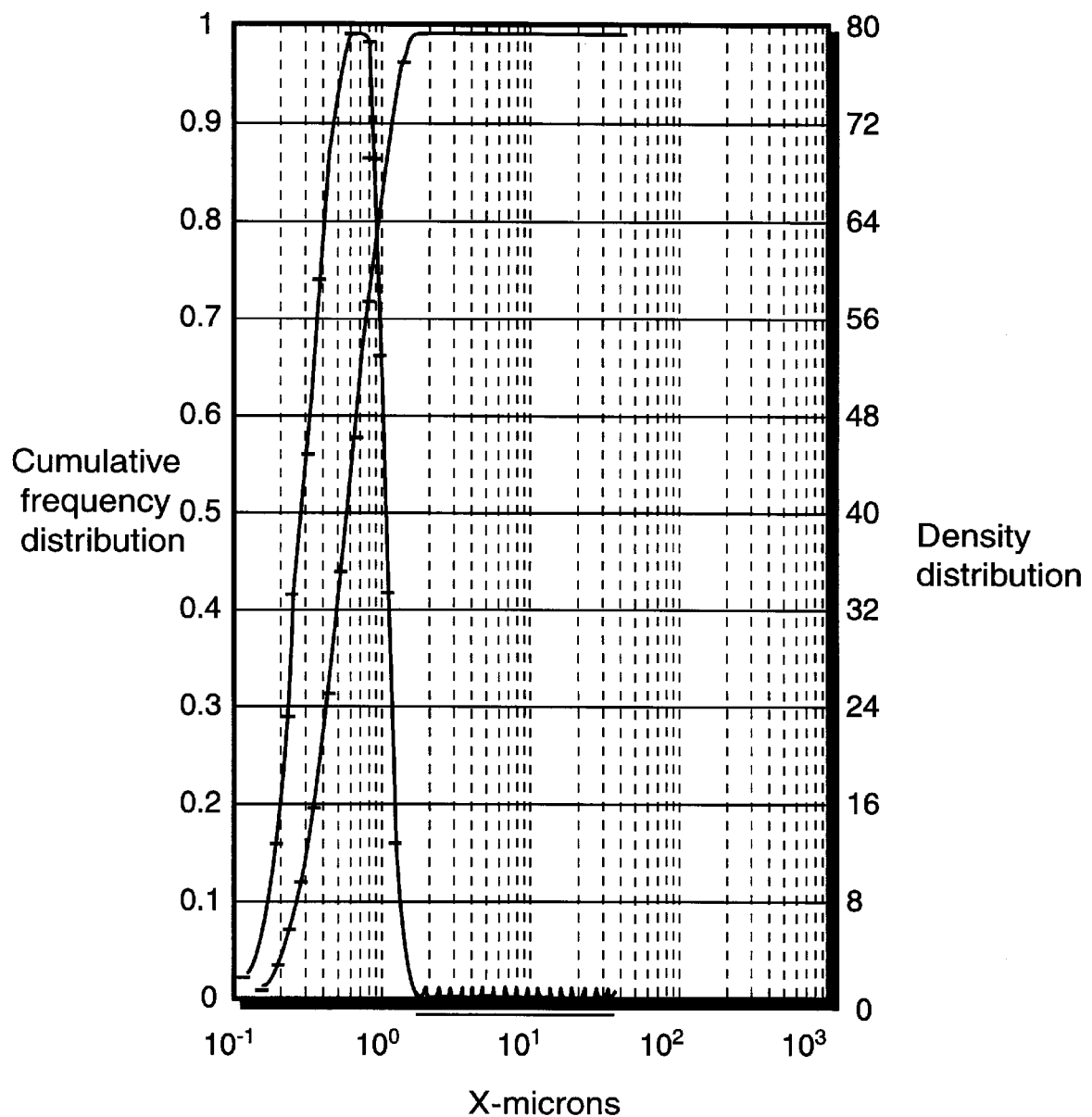
FIG. 1 is a graph showing the particle size distributions of shellac pseudolatices prepared in Example 1.

It is the object of the invention to provide a new process for the production of pseudolatices and micro or nanoparticles, in which especially no organic solvents need to be used and which is easy to carry out, whereby the pseudolatices or micro- or nanoparticles can be used in turn for the production of pharmaceutical preparations.

The object according to the invention is achieved by a process in which a polymer is heated to a temperature above its glass transition temperature and then high-pressure homogenized with water or an aqueous buffer solution, an then, if necessary, this suspension is converted into micro- and/or nanoparticles by drying.

Preferred versions of the process are the subject of the dependent claims.

Pseudolatices can, according to the invention, be produced by exploiting one important physical property of the polymers, the "change of state". Such physical properties of polymers are described in the general form in J. Brandrup und E. H. Immergut (publisher), Polymer Handbuch, 2nd edition, Wiley, New York (1975); D. W. van Krevelen, Eigenschaften von Polymeren, deren Abschätzung und Korrelierung mit der chemischen Struktur, 2nd edition, Elsevier, New York (1976).

The moment of the change of state of a polymer from solid to liquid or "soft" phase can be exploited for the production of pseudolatices by carrying out a homogenization in this phase, preferably a high-pressure homogenization.

Whilst a homogenization for the production of pseudolatices can only take place at the melting point or shortly before it in the case of crystalline polymers, various temperatures can be selected in the case of amorphous or partially crystalline polymers.

In the case of amorphous polymers such as for example polylactides, it is to be observed that maintaining lower temperature ranges suffices for the production of pseudolatices by means of homogenization, i.e. a slight softening of the polymers. In contrast to this, for polymers with small amorphous proportions such as for example shellac, higher temperatures or temperature ranges are required or need to be maintained respectively.

Considered especially as polymers are cellulose derivatives, poly(meth)acrylates, shellac, polylactides, polylactide/polyglycolide mixtures, polyhydroxybutyric acids or polycyanoacrylates.

The polymers are generally used in a quantity of 0.01 to 40 wt. %, preferably 0.1 to 20 wt. % and more preferably 1 to 15 wt. %, relative to the aqueous medium. A quantity of 10 wt. % is most preferred.

If necessary, high glass transition temperatures of polymers can be lowered by adding surfactants, suspension stabilisers and/or plasticizers, with the result that these polymers can also be used in aqueous systems for the production of pseudolatices. In general, they are used in a quantity of 0.05 to 10 wt. %, preferably 0.1 to 3 wt. % and most preferably 0.5 to 1 wt. %, relative to the aqueous medium in each case, the total quantity not exceeding 10 wt. % and preferably not 5 wt. %.

A second possibility for processing polymers with high glass transition temperatures involves, for example, increasing the boiling temperature of the aqueous medium by adding salts.

In addition, other usual auxiliaries can be added, such as for example preservatives, anti-oxidants or defoaming agents. All the auxiliaries can be added prior to heating and/or homogenization or also during homogenization.

The polymer used for the production of pseudolatices can, prior to heating and homogenization, be converted into a water-soluble form by changing the pH value, and then precipitated again from one such aqueous solution by changing the pH value again. In this way, pseudolatices can also for example be produced from acid polymers (e.g. shellac), initially by means of a precipitation of the shellac with acid after dissolution in alkali and only then by means of heating above the glass point and homogenization.

The production according to the invention of pseudolatices and micro- and/or nanoparticles is carried out in particular in the absence of organic solvents. The use of surfactants is advantageous here and takes place in particular to stabilize the suspension. Poloxamers, lecithins, foam inhibitors and wetting agents are preferably used as surfactants.

Medicaments can also be incorporated into the polymer so that pseudolatices or micro- or nanoparticles containing active ingredients can be produced. For this, the medicament is dissolved or suspended in the polymer prior to homogenization. According to a preferred version, A) the polymer is heated to a temperature above the glass transition temperature and B) the medicament (or several medicaments) is added and dissolved or suspended in the softened polymer. The medicament-containing polymer can then be left to cool, comminuted and sieved. The thus-produced particles (micro- or nanoparticles) preferably form a resuspendable powder. In this form, it can then be used in the process according to the invention for the production of pseudolatices and micro- or nanoparticles. Drying, comminution and sieving is however not absolutely essential. Rather, the softened medicament-containing polymer can also be homogenized directly in the aqueous medium.

If a medicament is added, it is preferably present in finely powdered form. The quantity of medicament is generally in the range 0.01 to 40 wt. %, preferably 0.1 to 30 wt. %, more preferably 0.5 to 20 wt. % and most preferably in the range from 1 to 15 wt. %, relative to the polymer.

The particle sizes of the pseudolatices are in the micrometer and/or nanometer range, whereby micro- and/or nanoparticles can result after drying, for example freeze- or spray-drying.

The micro- or nanoparticles produced by drying the homogenized polymer suspension are preferably likewise a resuspendable powder.

The surface of the polymer can also be modified by auxiliaries. This is preferably achieved by the sorption of block copolymers, proteins or glucoproteins. The polymer can also be coupled with antibodies. For this, the auxiliaries are used in a quantity of 1 ng to 1 mg per $cm^2$ of surface.

The pseudolatices or micro- or nanoparticles produced according to the invention are therefore suitable not only quite generally for the production of pharmaceutical preparations, but also for those in which the active ingredients can be controlled by changing suitable parameters such that a retarding release of the active ingredient is possible. Drug targeting is also possible.

The pseudolatices and micro- or nanoparticles can themselves be free of medicament and be used as coating materials for medicaments nuclei, or they can contain incorporated active ingredients. The pseudolatices according to the invention are particularly suitable for the production of diffusion films which can for example be used for the production of film tablets.

It is possible to incorporate a large number of active ingredients into the pseudolatices, micro- or nanoparticles. Preferably, the following active ingredient groups can be processed with the polymers as carrier materials:

hydroxylated hydrocarbons carbonyl compounds such as ketones (e.g. haloperidol), monosaccharides, disaccharides and amino sugars carboxylic acids such as aliphatic carboxylic acids, esters of aliphatic and aromatic carboxylic acids, basically-substituted esters of aliphatic and aromatic carboxylic acids (e.g. atropine, scopolamine), lactone (e.g. erythromycin), amides and imides of aliphatic carboxylic acids, amino acids, aliphatic amino carboxylic acids, peptides, polypeptides, β-lactam derivatives, penicillins, cephalosporins, aromatic carboxylic acids (e.g. acetyl salicylic acid), amides of aromatic carboxylic acids, vinylogous carboxylic acids and vinylogous carboxylic acid esters carbonic acid derivatives such as urethanes and thiourethanes, urea and urea derivatives, guanidine derivatives, hydantoins, barbituric acid derivatives and thiobarbituric acid derivatives nitro compounds such as aromatic nitro compounds and heteroaromatic nitro compounds amines such as aliphatic amines, aminoglycosides, phenylalkylamines, ephedrine derivatives, hydroxyphenyl ethanolamines, adrenalin derivatives, amphetamine derivatives, aromatic amines and derivatives and quaternary amino compounds sulphur-containing compounds such as thiols and disulphanes, sulphones, sulphonic acid esters and sulphonic acid amides polycarbocycles such as tetracyclines, steroids with aromatic ring A, steroids with α,β-unsaturated carbonyl function in ring A and α-ketol group (or methylketo group) at the $C_{17}$, steroids with a butenolide ring at the $C_{17}$, steroids with a pentadienolide ring at the $C_{17}$ and secosteroids O-containing heterocycles such as chromane derivatives (e.g. chromoglycinic acid)

N-containing heterocycles such as pyrazole derivatives (e.g. propyphenazone, phenyl butazone), imidazole derivatives (e.g. histamine, pilocarpine), pyridine derivatives (e.g. pyridoxine, nicotinic acid), pyrimidine derivatives (e.g. trimethoprime), indole derivatives (e.g. indometacin), lysergic acid derivatives (e.g.

ergotamine), yohimbine derivatives, pyrroloindole derivatives, purine derivatives (e.g. allopurinol), xanthine derivatives, 8-hydroxy quinoline derivatives, amino-hydroxy-alkylated quinolines, amino quinolines, isoquinoline derivatives (e.g. morphine, codeine), quinazoline derivatives, benzopyridazine derivatives, pteridine derivatives (e.g. methotrexate), 1,4-benzodiazepin derivatives, tricyclic N-containing heterocycles, acridine derivatives (e.g. ethacridine) and dibenzazepin derivatives (e.g. trimipramine)

S-containing heterocycles such as thioxanthene derivatives (e.g. chlorprothixene)

N,O— and N,S-containing heterocycles such as monocyclic N,O-containing heterocycles, monocyclic N,S-containing heterocycles, thiadiazine derivatives, bicyclic N,S-containing heterocycles, benzothiadiazine derivatives, tricyclic N,S-containing heterocycles and phenothiazine derivatives O,N,P-containing heterocycles (e.g. cyclophosphamide) inorganic compounds, such as ferrofluid ($Fe_3O_4$), magnetite and ions.

In general, the polymers for the production of pseudolatices are pounded, sieved (e.g. 90 $\mu$m), if necessary mixed with surfactants and dispersed in water. After dispersion, plasticizer, if desired, is added. There follow heating to various temperatures above the glass transition temperature and homogenization at various pressures, preferably high-pressure homogenization.

The following examples describe the invention in more detail.

EXAMPLE 1

Production of Shellac Pseudolatices 10 g sheet shellac are added to 50 ml water at 50 to 55° C. With portion-wise addition of solid NaOH (0.6 g) the preparation is stirred with a magnetic stirrer (900 rpm) until all the shellac has dissolved.

After dissolving the shellac, the shellac is precipitated with stirring (magnetic stirrer at 900 rpm), Ultra-Turrax treatment and portionwise addition of 50 ml 0.15 n-HCl. The particle sizes are up to 100 $\mu$m (measured by means of laser diffraction analysis, Sympatec, Clausthal-Zellerfeld).

This 10% shellac predispersion is mixed with 1% surfactant (Pluronic F 68, ICI Surfactants, Cleveland TSJE, England) and a few drops of anti-foaming emulsion (Wacker, Wacker-Chemie GmbH, Munich). Homogenization is carried out at 500 bar and various temperatures, with vigorous stirring. After high-pressure homogenization, the dispersion is stirred until cold and measured by means of laser diffraction analysis.

The shellac pseudolatices had different particle size distributions at the different temperatures which were used in each case during the high-pressure homogenization. It can be seen from Table 1 that high-pressure homogenization does not bring about a change in the particle size in each of the dispersions without any heating. Only heating into the start of the melting range (Table 1) led to a decrease in the particle sizes. A marked decrease was however achieved only at 90° C. (see volume distribution, FIG. 1).

On raising the pressure from 500 to 1000 bar during the high-pressure homogenization, a negligible change in the particle size in each of the shellac dispersions is to be observed (Table 2).

This shows that the temperature has a greater influence on the particle size of the shellac pseudolatices during the high-pressure homogenization than does the pressure.

The zeta potential measurement for the shellac dispersions gave values in the range from −42 to −47 mV. The result is a considerable repulsion of the particles from one another, which contributes to the stabilising of the dispersions produced.

General Points on Working in Active Ingredients

The polymer is heated above the glass point and thereby softened. The active ingredient is worked in in finely powdered form, whereby it can be present dissolved or suspended in the polymer matrix. After working in the active ingredient, the composition is pounded and sieved. Heating and homogenization are then carried out as mentioned above.

The release of the active ingredient from the polymer depends on the one hand on its solubility in water and on the other hand on its distribution in the polymer. Ferrofluid ($Fe_3O_4$), for example, has the property of remaining at a concentration of above 90% in the pseudolatices (D,L-polylactide) over several months.

EXAMPLE 2

Production of Polylactide Microparticles Containing Active Ingredient

The polymer (Resomer R 104, Boehringer Ingelheim) is heated in a flask in an oil bath into the melting range (80 to 100° C.). The diclofenacic acid is added in finely powdered form and the preparation is stirred by means of a stirrer for 5 minutes until the medicament is distributed homogeneously in the polymer. After cooling and therefore hardening of the polymer, the latter is comminuted, sieved (90 $\mu$m) and mixed with 1% (m/m) surfactant (Pluronic F 68). The preparation is dispersed in water, heated to 60° C. and high-pressure homogenized twice at both 500 bar and 1000 bar. The dispersion is then stirred until cold and immediately freeze-dried.

The particle size is determined by means of laser diffraction analysis. After producing the drug-loaded micro- and/or nanoparticles, a release test for the medicament is carried out in a paddle apparatus according to USP at a temperature of 37° C. and 100 rpm in phosphate buffer (pH 7.4). The concentration of the medicament is determined photometrically over 8 hours.

Figure 2:
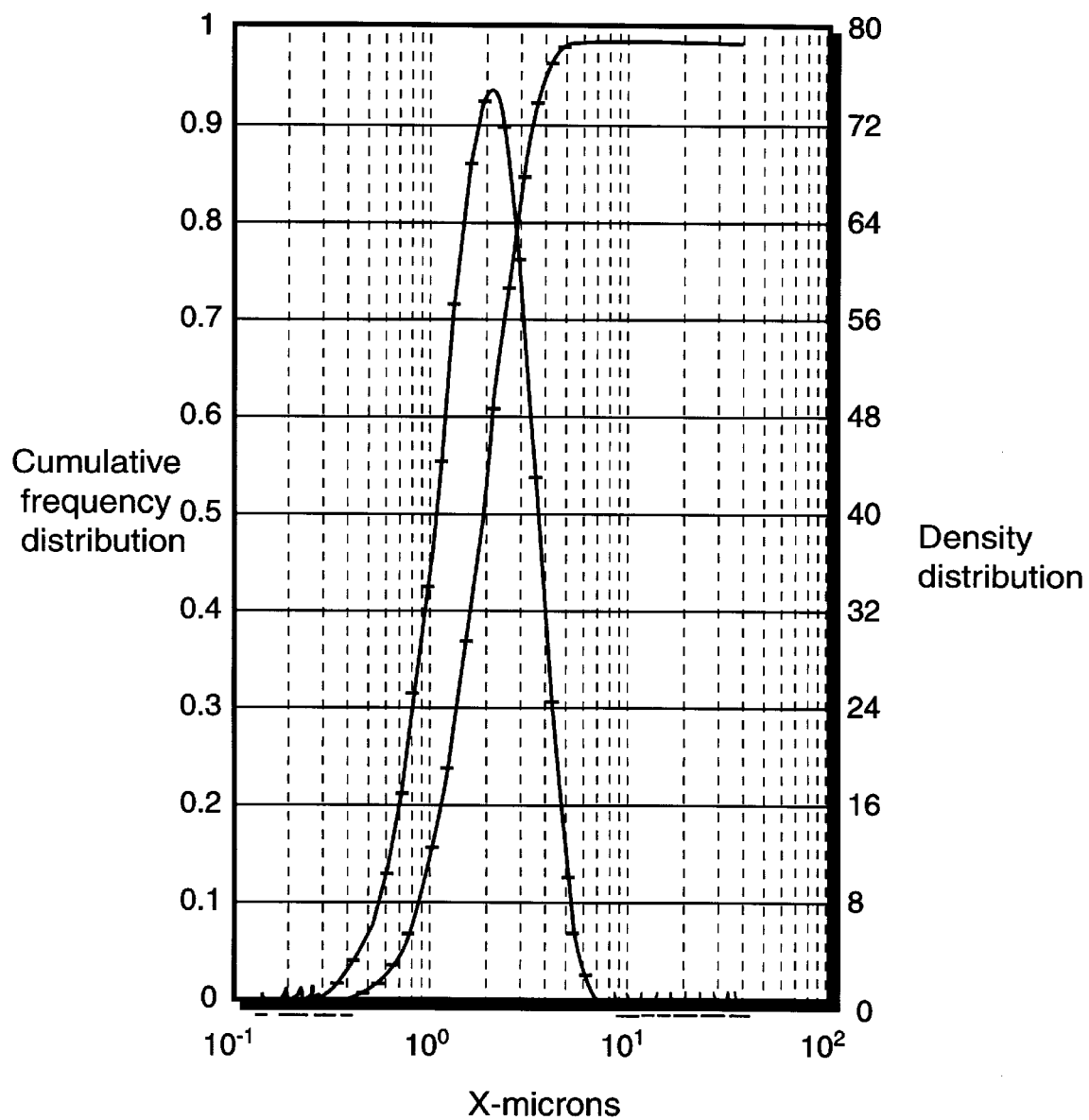
FIG. 2 is a graph showing particle size distribution of polylactide pseudolatices prepared in Example 2.

The particle size distribution for D,L-polylactide after working in the medicament can be seen from FIG. 2. As with shellac, it is also shown here that increasing the pressure does not bring about any reduction in the particle size.

Figure 3:
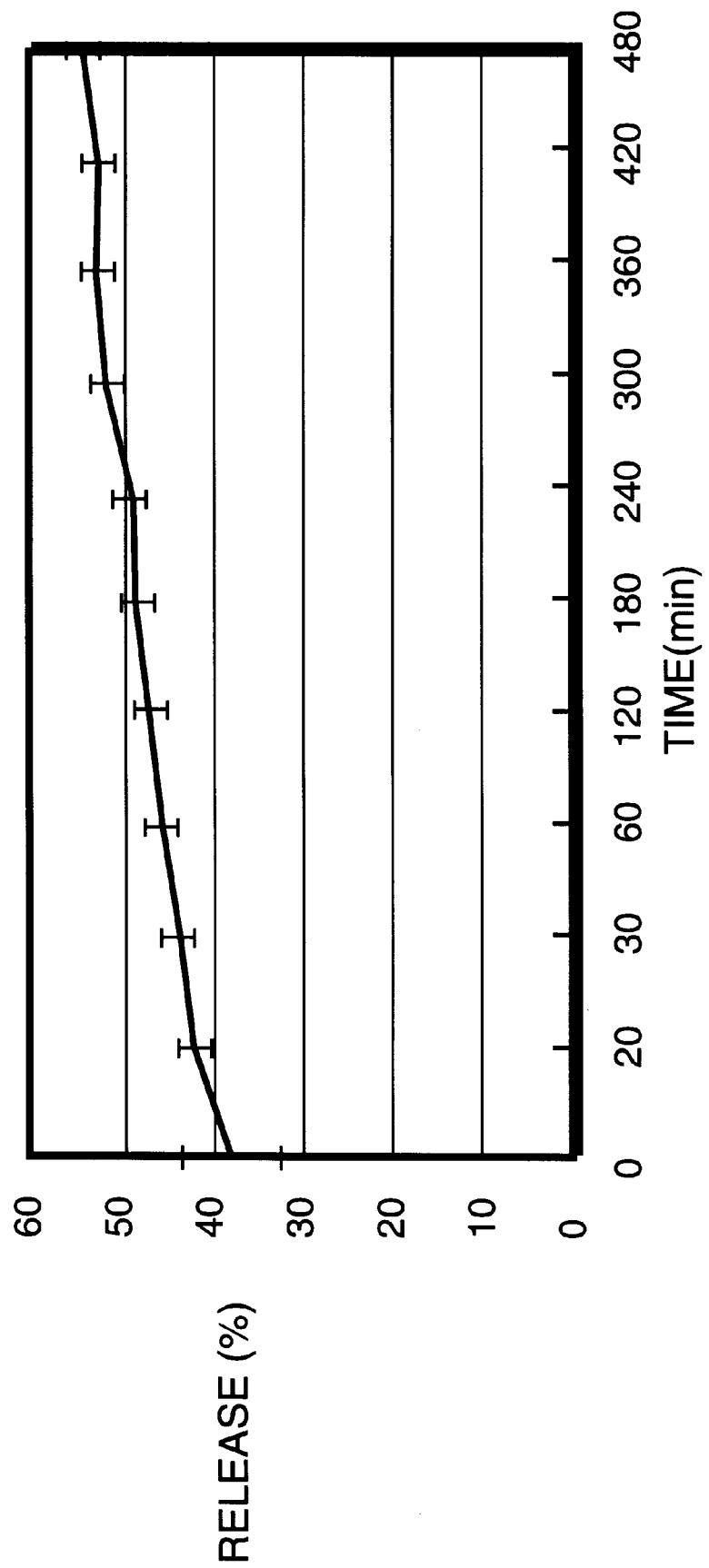
FIG. 3 shows the percent release medicament over time from particles prepared in Example 2.

The release of the medicament from the polylactide shows a strongly retarding pattern (FIG. 3). The undesired effect whereby a certain concentration of medicament is already released at the start because there is a proportion of the medicament on the surface of the particle, can be avoided by washing the particle with, for example, water.

Since, in this method of producing pseudolatices and micro- and/or nanoparticles, the polymers are dispersed in water and heated above the glass point or the melting point, the boiling temperature of water presents itself as the limiting factor. Polymers which can have a high glass transition temperature or a higher melting point than the boiling temperature of water cannot be processed in this way to give pseudolatices and micro- and/or nanoparticles. One possibility of processing polymers with high glass transition temperatures according to this method is, as mentioned above, to add plasticizers which have the property of lowering the glass transition temperature, or adding salts which raise the boiling temperature of the medium.

EXAMPLE 3

Production of Ethyl Cellulose Pseudolatices 4.25 g ethyl cellulose, 0.5 g sodium dodecyl sulphate, 0.5 g Pluronic F 68, 0.5 g cetyl alcohol and 1 g diethyl phthalate are added to 50 ml water. After heating above 60° C., high-pressure homogenization is carried out, initially twice at 100 bar, once at 250 bar and once at 500 bar. Pseudolatices with a broad particle size distribution between 0.1 and 20 μm are produced. Through the addition of 20% diethyl phthalate to the ethyl cellulose, a lowering of the glass point from 125° C. to 60° C. is achieved.

TABLE 1

High-pressure homogenization at various temperatures and particle sizes at 500 bar

| Temperature (°C.) | Particle size (μm) |
|---|---|
| 20 | up to 100 |
| 60 | up to 40 |
| 70 | up to 32 |
| 80 | up to 28 |
| 90 | up to 2 |

TABLE 2

High-pressure homogenization at various temperatures and particle sizes at 100 bar

| Temperature (°C.) | Particle size (μm) |
|---|---|
| 20 | up to 100 |
| 60 | up to 42 |
| 70 | up to 36 |
| 80 | up to 26 |
| 90 | up to 2 |

We claim:

1. A process for the production of pseudolatices and micro- and/or nanoparticles, comprising the steps of:

(a) heating and softening a crystalline, partially crystalline or amorphous polymer selected from the group consisting of cellulose derivatives, poly (meth)acrylates, shellac, polylactides, polylactide/polyglycolide mixtures polyhydroxy butyric acids and polycyanoacrylates to a temperature above its glass transition temperature and below its melting point, and then (b) at a pressure of about 100 to about 1,000 bar homogenizing the heated, softened polymer in an aqueous medium which is water or an aqueous buffer solution to form a suspension and, optionally (c) drying the suspension and recovering the micro- and/or nanoparticles.

2. The process according to claim 1 wherein 0.01 to 30 wt. % polymer, relative to the aqueous medium, is used.

3. The process according to claim 1 wherein surfactants, suspension stabilizers and/or plasticizers are added to the aqueous medium.

4. The process according to claim 3 wherein the total quantity of surfactant, suspension stabilizer or plasticizer is in the range from 0.05 to 10 wt %, relative to the aqueous medium.

5. The process according to claim 1 wherein preservatives, antioxidants or defoaming agents are added prior to step (a) or (b) or during step (b).

6. The process according to claim 1, wherein prior to heating and homogenization, the polymer is converted into a water soluble form by changing the pH value and then precipitated from an aqueous solution by changing the pH value again.

7. The process according to claim 1 wherein at least one medicament is incorporated into the polymer.

8. The process according to claim 7, wherein the medicament is dissolved or suspended in the polymer prior to homogenization.

9. The process according to claim 8 wherein the medicament is worked into the polymer, prior to homogenization, by:

(1) heating and softening the polymer to a temperature above its glass transition temperature and below its melting point, (2) adding the medicament and dissolving or suspending it in the softened polymer, and then (3) allowing the medicament-containing polymer to cool, comminuting it and sieving it.

10. The process according to claim 1 wherein the micro- and/or nanoparticles are dried in step (c) by freeze- or spray-drying.

11. The process according to claim 1 wherein the surface of the polymer is modified to provide block copolymers, proteins or glucoproteins thereon.

12. The process according to claim 1 wherein the polymer has antibodies coupled to it.

* * * * *